United States Patent
Libby et al.

(10) Patent No.: US 8,603,008 B2
(45) Date of Patent: Dec. 10, 2013

(54) APPARATUS FOR GENERATING AND COLLECTING SALIVA SAMPLES CONTAINING ENHANCED CELL CONCENTRATIONS

(75) Inventors: Brian Joseph Libby, Hingham, MA (US); Paul D. Slowey, Vancouver, WA (US)

(73) Assignee: Oasis Diagnostics Corporation, Vancouver, WA (US)

( * ) Notice: Subject to any disclaimer, the term of this patent is extended or adjusted under 35 U.S.C. 154(b) by 0 days.

(21) Appl. No.: 12/755,386

(22) Filed: Apr. 6, 2010

(65) Prior Publication Data
US 2010/0331725 A1 Dec. 30, 2010

Related U.S. Application Data

(60) Provisional application No. 61/167,110, filed on Apr. 6, 2009.

(51) Int. Cl.
*A61B 5/00* (2006.01)

(52) U.S. Cl.
USPC ............................................. 600/573

(58) Field of Classification Search
USPC ............. 600/573, 575–578; 606/234, 236; 433/91
See application file for complete search history.

(56) References Cited

U.S. PATENT DOCUMENTS

| | | | | |
|---|---|---|---|---|
| 4,335,730 A * | 6/1982 | Griffin | ............ | 600/573 |
| 4,589,548 A * | 5/1986 | Fay | ............ | 206/363 |
| 4,685,472 A * | 8/1987 | Muto | ............ | 600/573 |
| 4,761,379 A * | 8/1988 | Williams et al. | ............ | 600/573 |
| 4,813,931 A * | 3/1989 | Hauze | ............ | 604/540 |
| 4,951,684 A * | 8/1990 | McMillan | ............ | 600/571 |
| 5,569,210 A * | 10/1996 | Moen | ............ | 604/191 |
| 5,720,299 A * | 2/1998 | Theodoru | ............ | 600/573 |
| 5,910,122 A * | 6/1999 | D'Angelo | ............ | 600/573 |
| 5,919,146 A * | 7/1999 | Propp | ............ | 600/577 |
| 6,022,326 A * | 2/2000 | Tatum et al. | ............ | 600/573 |
| 6,200,276 B1 * | 3/2001 | Biesel et al. | ............ | 600/573 |
| 7,282,181 B2 * | 10/2007 | Hudak et al. | ............ | 422/549 |
| 7,335,023 B2 * | 2/2008 | Mahlmann | ............ | 433/96 |
| 7,845,944 B2 * | 12/2010 | DiGasbarro | ............ | 433/91 |
| 7,943,382 B2 * | 5/2011 | Sekine et al. | ............ | 436/63 |
| 7,955,318 B1 * | 6/2011 | Schultz et al. | ............ | 604/540 |
| 2003/0021736 A1 * | 1/2003 | Kang et al. | ............ | 422/102 |
| 2003/0064526 A1 * | 4/2003 | Niedbala et al. | ............ | 436/165 |
| 2004/0260194 A1 * | 12/2004 | Bayer et al. | ............ | 600/529 |
| 2005/0096563 A1 * | 5/2005 | Liang | ............ | 600/573 |
| 2006/0149164 A1 * | 7/2006 | Lee et al. | ............ | 600/573 |
| 2009/0012425 A1 * | 1/2009 | Dodge et al. | ............ | 600/572 |

* cited by examiner

*Primary Examiner* — Max Hindenburg
(74) *Attorney, Agent, or Firm* — Mark E. Beatty; Kurt M. Rylander; Rylander & Associates P.C.

(57) ABSTRACT

An apparatus for generating and collecting saliva samples containing enhanced cell concentrations includes a mouthpiece having a mouth contact portion and a flow channel which may include a tapered basin, a conduit in fluid communication with the flow channel, and one or more collectors couplable to the conduit. The mouth contact portion and basin may be textured to enhance cell removal. The mouth contact portion may include a plurality of internal and external channels disposed around the flow channel. Filters may be included between the flow channel and the collectors. A closure member is provided.

16 Claims, 10 Drawing Sheets

APPARATUS FOR GENERATING AND COLLECTING SALIVA SAMPLES CONTAINING ENHANCED CELL CONCENTRATIONS

CROSS-REFERENCE TO RELATED APPLICATION

This application claims priority to U.S. Provisional Patent Application Ser. No. 61/167,110 filed Apr. 6, 2009, which is hereby incorporated by reference.

FIELD OF THE INVENTION

The present invention relates to saliva sample collection devices. More specifically, the present invention relates to apparatus and methods for generating and collecting saliva samples containing enhanced concentrations of cells from the test subject.

BACKGROUND

Saliva sampling for use in genetic testing is becoming increasingly common. This is true because saliva naturally contains some cells, such as buccal cells, for example, and saliva generally is easier to obtain and/or work with than is most other sources of cells, including blood and hair, for example. One drawback to using saliva as a source of genetic material in a genetic application, however, is that not all saliva samples contain a sufficient number of cells to provide the genetic material that is required to complete the application. For example, perhaps about 1-50 µg of DNA can be isolated from 2 ml of saliva that naturally exists in the human mouth. This amount is insufficient for analysis of a genome that involves several thousand separate polymerase chain reactions, an amount of such reactions that is sometimes performed in the analysis of a genome. Further, of the 1-50 µg of DNA obtained, perhaps about 10% is from one or more bacterial species that are normally present in the mouth (such as *Streptococcus mutans* and certain *Lactobacillus* species, for example). This contaminating bacterial DNA can lead to failed assays and, worse, to misleading results.

Many devices have been developed for collecting saliva to test for presence of particular antibodies and antigens, such devices are unsuitable for DNA and RNA testing regimes, because these devices do not collect a sufficient amount of recoverable cell and cellular material to be used for large scale testing or field testing. Although it is known that increasing cell concentrations in saliva samples would be useful, and devices are being developed for collecting cell materials by scraping mucous surfaces to collect tissue, Applicant is unaware of a practical method or apparatus which are useful in the field, on a large scale, which can produce and collect saliva fluid samples with enhanced concentrations of cells from the test subject for genetic or other cell-based testing. The distinction is important because, while tissue samples are useful for certain applications and testing scenarios, saliva fluid samples are easier preserve and ship to testing labs from field locations with limited facilities. For example, devices which scrape tissue to accumulate cellular material require a substantially larger volume of buffer fluid, which is relatively expensive to obtain and ship, to preserve the sample retained on the scraping device, and testing requires a step of removing the cell material from the scraper prior to evaluating the sample. Saliva fluid samples, by contrast, merely require the addition of small amount of buffer solution—a few drops for a 2 ml sample of saliva, for example—and do not require the additional step of removal from the scraper.

Additionally, existing devices for collecting fluid samples are awkward to use for both the tester and the subject as they generally require spitting or drooling into a separate collection cup of some sort. This is both annoying (which impacts participation of subjects), unsanitary, and creates the potential for contamination of samples.

In certain circumstances, it is important to filter debris from the collected specimen in order to be able to extract Ribonucleic Acid [RNA] from the sample or simply to remove large particles.

What is needed therefore is a saliva sample collection device that is optimally arranged to increase cell concentration with respect to the cell concentration that is normally present in saliva sample. Further, the needed saliva sample collection device should be user friendly, simple to operate and sanitary for use so that members of the public, as well as healthcare professionals may use the device effectively.

SUMMARY AND ADVANTAGES

An apparatus for generating and collecting saliva samples containing enhanced cell concentrations is provided which includes a mouthpiece with a contact portion that operates against the interior surfaces of a subject's mouth to release cells which are then collected through discharge of liquid saliva from the subject. The contact portion includes a flow channel to direct saliva to a collector, and may include texturing to increase release of cells from tissue surfaces. The mouthpiece may include a tapered basin which allows a subject to retain the apparatus in the mouth during collection, or remove the apparatus after agitation and then spit or drool into the collector. The apparatus may incorporate filters and preservation materials to preserve and enhance the usefulness of the collected sample. Multiple collectors may be used simultaneously.

The apparatus of the present invention presents numerous advantages, including: (1) facilitation of the collection of a fluid in sufficient quantity and with sufficient amount of cellular material to conduct genetic testing and any other testing requiring DNA or RNA; (2) inexpensive construction; (3) sealing feature to substantially protect the collected fluid sample; (4) rapid sample collection time; (5) simple and more elegant collection method than traditional "spit-in-a-cup" technologies; (6) more amenable for large population studies and DNA collection by the patient/subject in the home; (7) rapid collection time reduces the possibility for introduction of any "foreign" DNA; (8) incorporation of a preservative or lysis buffer capable of protecting the integrity of the sample for long periods of time; and, (9) ability to collect samples with the subject's head remaining upright; (10) ability to collect samples from animals.

Additional advantages of the invention will be set forth in part in the description which follows, and in part will be obvious from the description, or may be learned by practice of the invention. The advantages of the invention may be realized and attained by means of the instrumentalities and combinations particularly pointed out in the appended claims. Further benefits and advantages of the embodiments of the invention will become apparent from consideration of the following detailed description given with reference to the accompanying drawings, which specify and show preferred embodiments of the present invention.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

REFERENCE NUMBERS USED IN DRAWINGS

Turning now descriptively to the drawings, in which similar reference characters denote similar elements throughout the several views, the figures illustrate the fluid sample collection system of an embodiment of the present invention. With regard to the reference numerals used, the following numbering is used throughout the various drawing figures:

NUMBER DESCRIPTION

10 Saliva sample
100 First embodiment
105 Flow channel
110 Mouthpiece
111 Basin
112 Mouth contact portion
113 Conduit
114 First contact surface
115 Second contact surface
116 Third contact surface
117 Basin interior surface
118 Surface texturing ridges
120 Collector
124 Mating port
125 Conduit interior channel
130 Closure member
131 Closure member second portion
132 Closure member first portion
133 Plastic wrap tear away region
200 Mouth
210 Teeth
220 Interior cheek
230 Lips
240 Gums
250 Tongue
300 Second embodiment
305 Flow channel
310 Mouthpiece
311 Basin
312 Mouth contact portion
314 First contact surface
315 Second contact surface
316 Third contact surface
317 Basin interior surface
319 Internal channel
320 Collector
322 External channel
400 Third embodiment
405 Flow channel
410 Mouthpiece
412 Mouth contact portion
413 Conduit
414 First contact surface
415 Second contact surface
416 Third contact surface
420 Collector
424 Mating port
500 Fourth embodiment
505 Flow channel
510 Mouthpiece
512 Mouth contact portion
513 Conduit
514 First contact surface
515 Second contact surface
516 Third contact surface
520 Collector
524 Mating port
528 Preservation material
600 Fifth embodiment
605 Flow channel
610 Mouthpiece
611 Basin
612 Mouth contact portion
613 Conduit
614 First contact surface
615 Second contact surface
616 Third contact surface
617 Basin interior surface
620a First collector
620b Second collector
623a First collector channel wall
623b Second collector channel wall
624a First mating port
624b Second mating port
625 Conduit internal channel
629a First collector channel
629b Second collector channel
640a First filter
640b Second filter

DETAILED DESCRIPTION

Before beginning a detailed description of the subject invention, mention of the following is in order. When appropriate, like reference materials and characters are used to designate identical, corresponding, or similar components in differing figure drawings. The figure drawings associated with this disclosure typically are not drawn with dimensional accuracy to scale, i.e., such drawings have been drafted with a focus on clarity of viewing and understanding rather than dimensional accuracy.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Referring to FIGS. 1-10, a saliva sample collection device is provided, and includes comprising: a mouthpiece having a mouth contact portion including an outer contact surface, and a flow channel through said mouthpiece; a conduit coupled to said mouthpiece, said conduit having an interior channel in fluid communication with said flow channel; and, one or more collectors coupled to said conduit. A saliva sample collection device includes wherein said conduit further comprises, and each of said one or more collectors is removably couplable to said conduit. A saliva sample collection device includes a mouthpiece having a mouth contact portion including an outer contact surface, and a flow channel through said mouthpiece; a conduit coupled to said mouthpiece, said conduit including an interior channel in fluid communication with said flow channel and one or more mating ports in fluid communication with said conduit interior channel; and, wherein each of said one or more mating ports is also removably couplable to a collector. A saliva sample collection device includes one or more collectors corresponding to said one or more mating ports, each of said one or more collectors removably couplable to a corresponding mating port. A saliva sample collection device includes wherein said flow channel comprises a basin having an interior surface tapering from said outer contact surface inward to said conduit. A saliva sample collection device includes wherein outer contact surface includes texturing. A saliva sample collection device includes wherein said texturing includes a plurality of parallel ridges. A saliva sample collection device includes wherein said basin interior surface includes texturing. A saliva sample collection device includes wherein said mouth contact portion outer surface includes at least opposing front and back contact surfaces, and said mouth contact portion further includes a plurality of internal channels extending through said mouth contact portion from said front contact surface to said back contact surface, said internal channels disposed around said flow channel. A saliva sample collection device includes wherein said mouth contact portion outer surface includes a plurality of external channels disposed around said flow channel. A saliva sample collection device includes wherein said one or more mating ports comprises a plurality of mating ports, and said conduit includes a plurality of collector channels corresponding to said plurality of mating ports, each of said plurality collector channels extending within at least a portion of said conduit interior channel, each of said plurality of collector channels in fluid communication with said conduit interior channel and one of said plurality of mating ports. A saliva sample collection device includes a filter disposed between said mouthpiece flow channel and said one or more collectors, said filter in fluid communication with said conduit internal passage and said one or more mating ports. A saliva sample collection device includes wherein a plurality of filters corresponding to said plurality of mating ports, each of said filters disposed between a corresponding collector channel and a corresponding collector. A saliva sample collection device includes a preservation material disposed in at least one of said one or more collectors. A saliva sample collection device includes a closure member, said closure member including a first portion sealingly insertable into said conduit and a second portion enclosing said mouthpiece. A saliva sample collection device includes a mouthpiece having a mouth contact portion and a flow channel through said mouthpiece, wherein said mouth contact portion further comprises a textured outer contact surface, and said flow channel further comprises a basin having a textured interior surface tapering from said outer contact surface inward to said conduit; a conduit coupled to said mouthpiece, said conduit including an interior channel in fluid communication with said flow channel and one or more mating ports in fluid communication with said conduit interior channel; and, one or more collectors corresponding to said one or more mating ports, each of said one or more collectors removably couplable to a corresponding mating port, and at least one filter disposed between said flow channel and at least one of said one or more collectors.

Referring to FIGS. 1-6, a first embodiment of a saliva sample collection device 100 is shown, including a mouthpiece 110 having an mouth contact portion 112 including an outer surface 114, 115 and 116, and a flow channel 105 through mouthpiece 110; a conduit 113 coupled to mouthpiece 110 and having an interior channel 125 in fluid communication with flow channel 105; and, a collector 120 coupled to conduit 113 at its end distal from mouthpiece 110. In the embodiment conduit 113 includes a mating port 124 and collector 120 is removably coupled to mating port 124. In the embodiment flow channel 105 forms a conical basin 111 having an interior surface 117 surrounded by mouth contact portion 112 which tapers inwardly to flow channel 105 to facilitate collection of saliva by spitting or drooling into basin 111. Flow channel 105 with basin 111 is in fluid communication with collector 120 through conduit interior channel 125 and mating port 124 when collector 120 is coupled to mating port 124.

Figure 1:
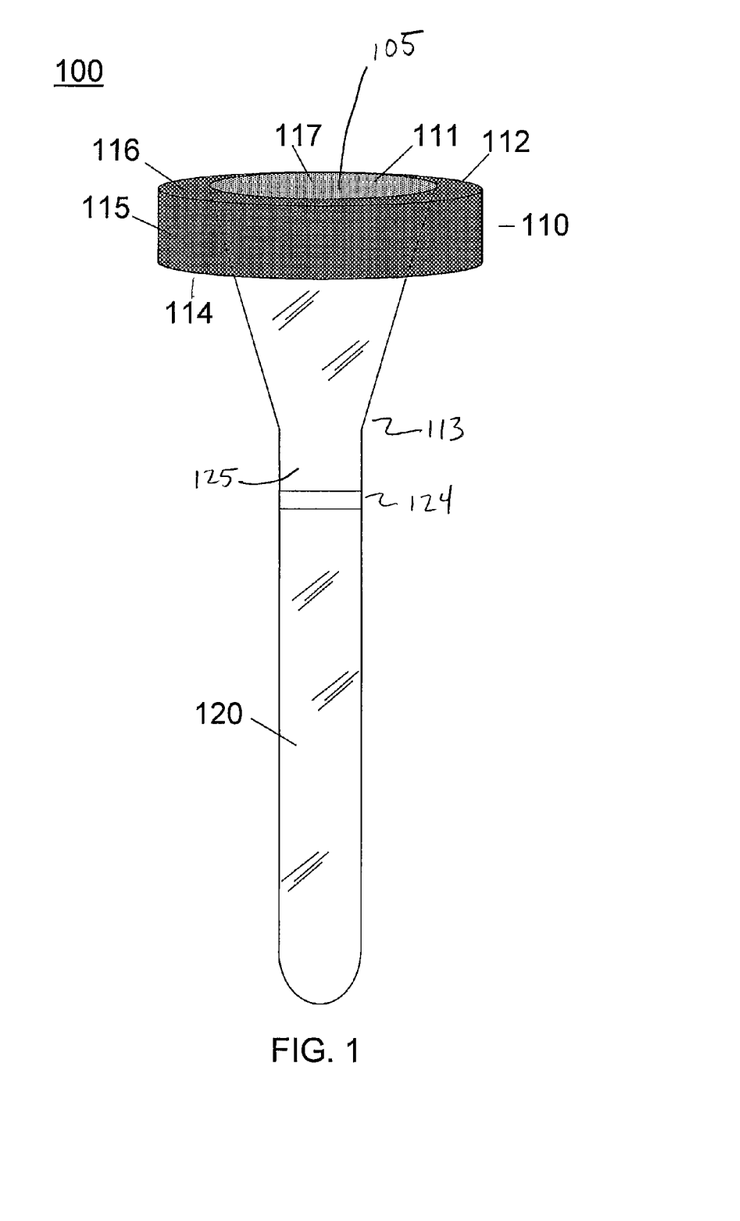
FIG. 1 shows a side view of a first embodiment of a saliva sample collection device.
Figure 2:
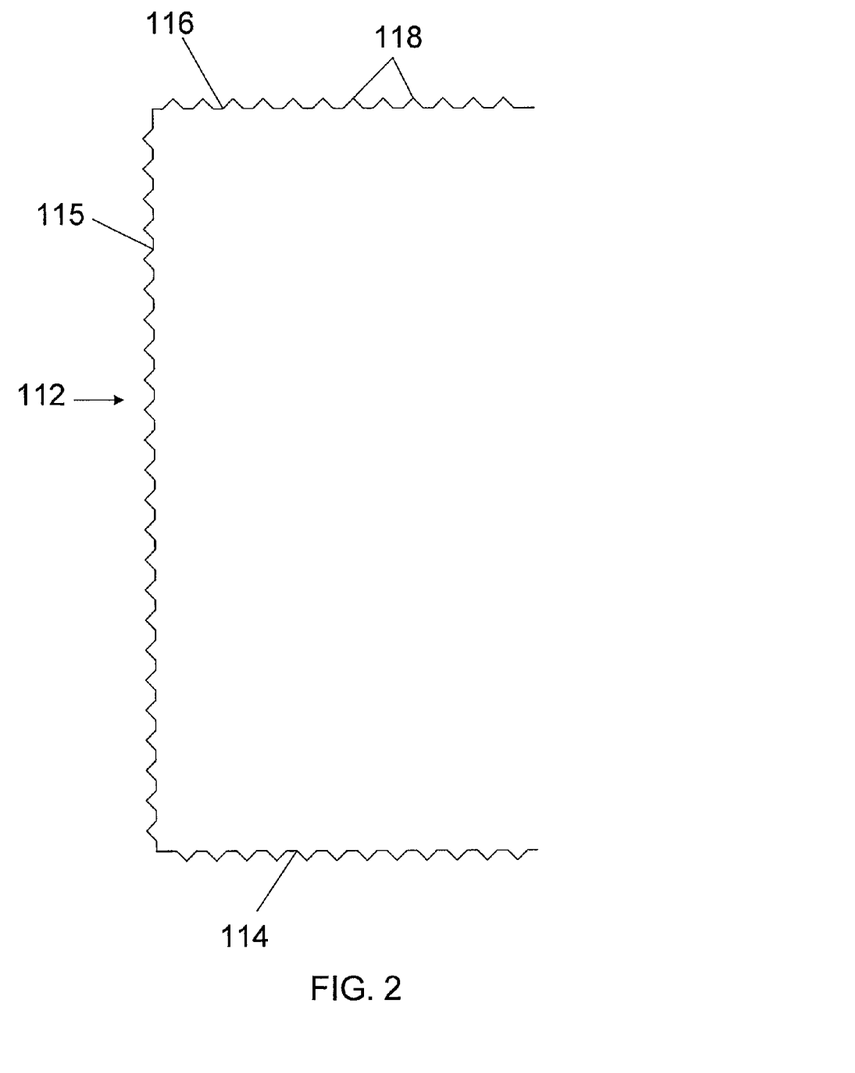
FIG. 2 shows a cross-sectional view of a mouth contact portion of a first embodiment.
Figure 3A:
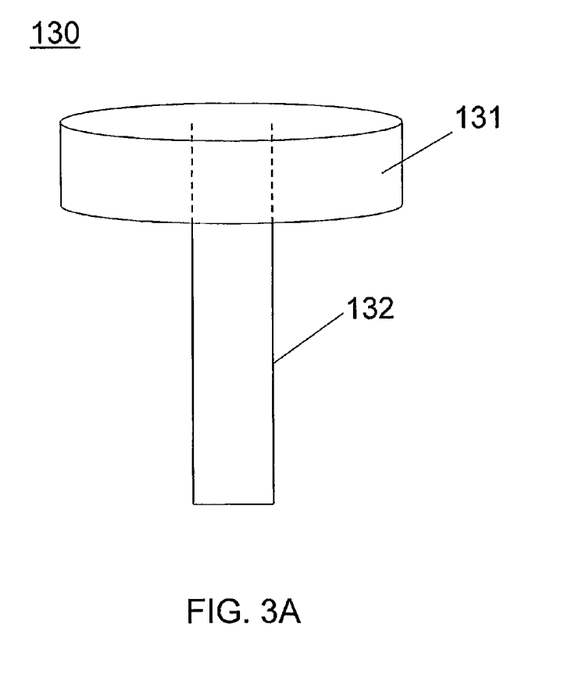
FIG. 3A shows a side view of a closure member of a first embodiment.
Figure 3B:
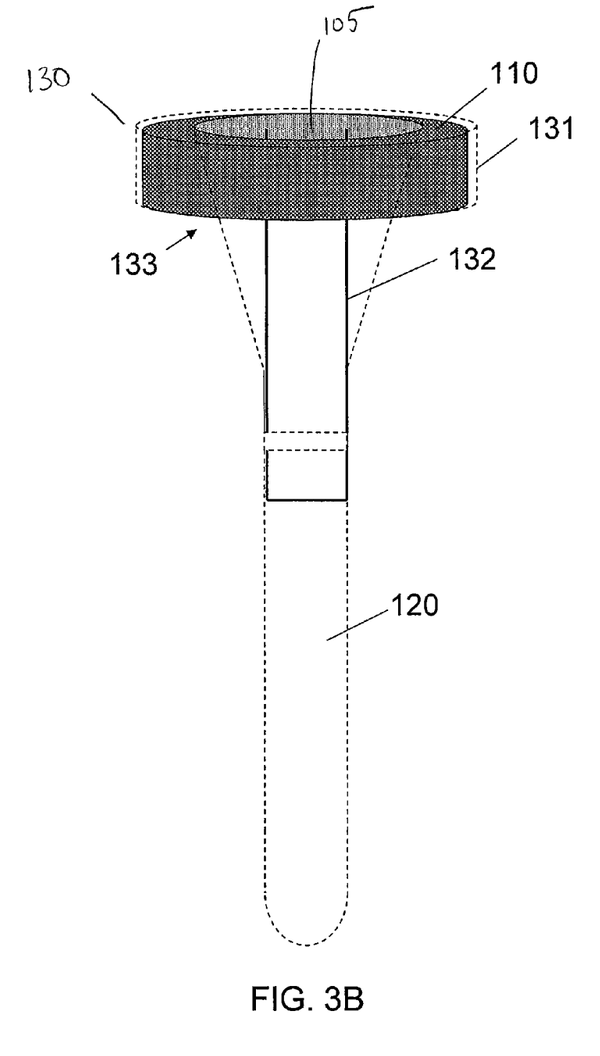
FIG. 3B shows a side view of a first embodiment with a closure member installed.

In the embodiment, contact portion 112 includes first, second and third contact surfaces 114, 115 and 116, respectively, which include ridges 118 to increase release of buccal cells from cheek and gum surfaces. Contact surfaces 114, 115 and 116 may form a continuous contact surfaces without sharp edges there between, or separate and distinct surfaces. First contact surface 114 and third contact surface 116 form opposing back and front contact surfaces, respectively. Second contact surface 115 may vary in width, depending on the anticipated dimensions of the test subject's mouth. In the embodiment second contact surface 115 is approximately 1-2 cm wide. In the embodiment, contact portion 112 is a substantially a circular annulus with a rectangular cross section, as shown in FIG. 2, but the annulus could be polygonal as well. In the embodiment, the interior surface 117 of basin 111 is also textured in order to increase removal of cells from the tongue and to stimulate saliva production.

Collector 120 may be made from any suitable material, and any suitable size or shape, as determined by the needs of the user. Any number of collector types are available and may be used, depending on the needs of the user. By way of example only, CORNING® 15 mL Polypropylene Centrifuge Tube, a CORNING® 2 mL External Threaded Polypropylene Cryogenic Vial, a CORNING® 50 mL Polypropylene Centrifuge Tube, or a PYREX® 10×75 mm Disposable Rimless Culture Tube; each one these products is commercially available from Corning Incorporated of Corning, N.Y. (Corning Product Nos. 430790, 430289, 430897, and 99445-10, respectively).

Referring to FIGS. 3A, 3B, 5 and 6, a closure member 130 closure member 130 is provided, including first portion 132 which is sealing insertable into conduit 113 to form a plug, and a second portion 131 which encloses mouthpiece 110.

Figure 7:
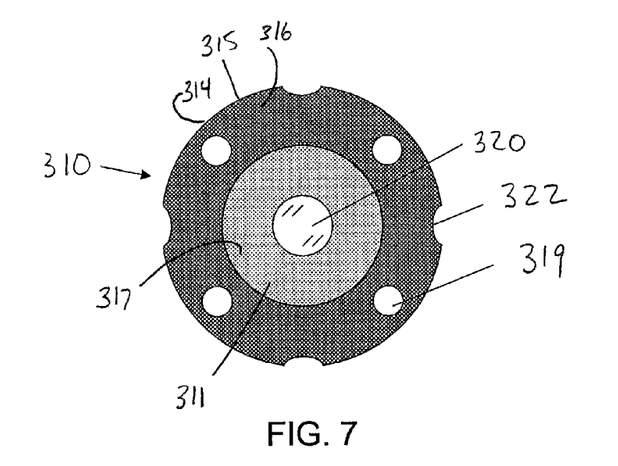
FIG. 7 shows an end-on view of a second embodiment.

Referring to FIG. 7, a second embodiment is shown. In the embodiment, mouthpiece 310 includes contact portion 312 having at least opposing front and back contact surfaces 316 and 314, respectively, and a plurality of internal channels 319 extend through mouth contact portion 312 from front surface 316 to back surface 314. In the embodiment mouth contact portion contact surface 314, 315 and 316 includes a plurality of open external channels 322, which are primarily formed along outside contact surface 315. External channels 322 assist in agitation of mouth surfaces to release cells and also allow freer flow toward flow channel 305. Internal channels 319 and external channels 322 are disposed around flow channel 305 to allow saliva fluid generated along contact surfaces 314 and 315 to flow through to flow channel 305 and for collection in collector 320. Internal passages 319 and external channels 322 also provide improved saliva flow between a portion of the mouthpiece that movably contacts the inner cheek region 220, where maximum dissociation of buccal cells is expected to occur, and the area at or around the tongue 250, where saliva is generated.

Figure 8:
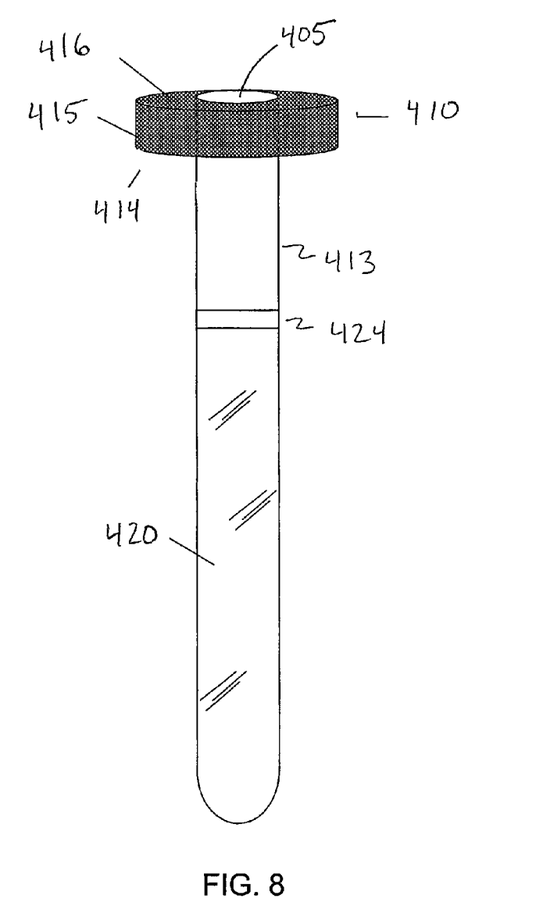
FIG. 8 shows a side view of a third embodiment.

Referring to FIG. 8, a third embodiment is shown. Mouthpiece 410 includes first, second and third contact surfaces 414, 415 and 416, respectively, flow channel 405 in fluid communication with conduit 413, and collector 420 removably connected to conduit 413. First, second and third contact surfaces 414, 415 and 416 are textured to maximize buccal cell displacement.

Figure 9:
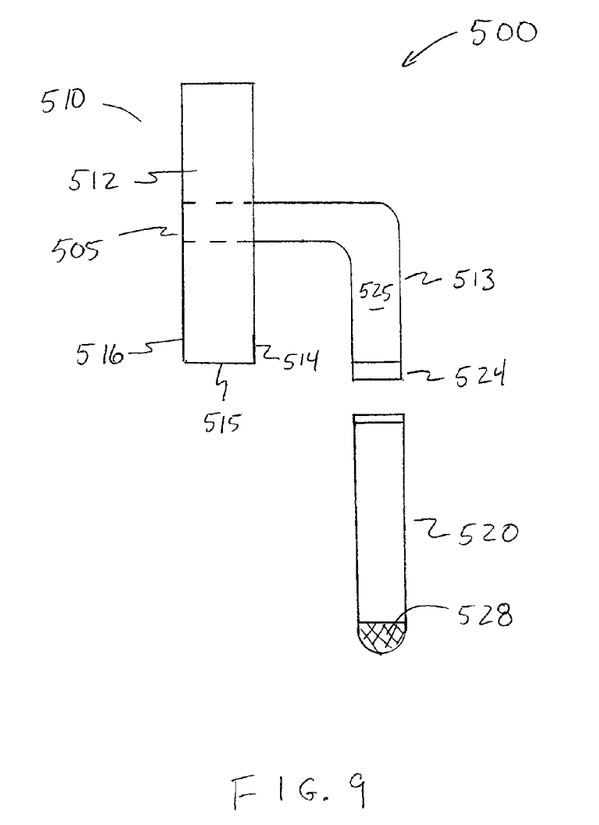
FIG. 9 shows a side view of a fourth embodiment.

Referring to FIG. 9, a fourth embodiment 500 is shown, including mouthpiece 510 having a mouth contact portion 512 with first, second and third contact surfaces 514, 515 and 516, and flow channel 505 in fluid communication with conduit 513. Conduit 513 extends out from mouthpiece 510 away from a subject's mouth, and includes mating port 524 at its end distal from mouthpiece 510. Collector 520 is removably coupled to conduit 513 through mating port 524. In the embodiment, conduit 513 is bent so that the subject can maintain his head vertical while saliva accumulates in collector 520. Collector 520 is preloaded with sample preservation material 528, to preserve and/or prepare the sample 10. Preservation material may include one or more suitable agents, in liquid, solid or powdered form, for preserving, stabilizing, treating or otherwise providing benefit to the collected cells and/or the contents thereof (for example, DNA, RNA, and protein). For example, A suitable nucleic acid stabilizing agent is a solution of 1% sodium dodecyl sulfate (w:v), 1.0 mM EDTA, and 10 mM TRIZMA™ Base in deoxyribonuclease-free and ribonuclease-free deionized and distilled water (optionally sterilized by passing the solution through a 0.2 µM filter, for example). The use of pre-loaded preservation material simplifies large scale sample collections in the field and reduces the risk of contamination or sample loss from adding agents after sample collection.

Figure 10:
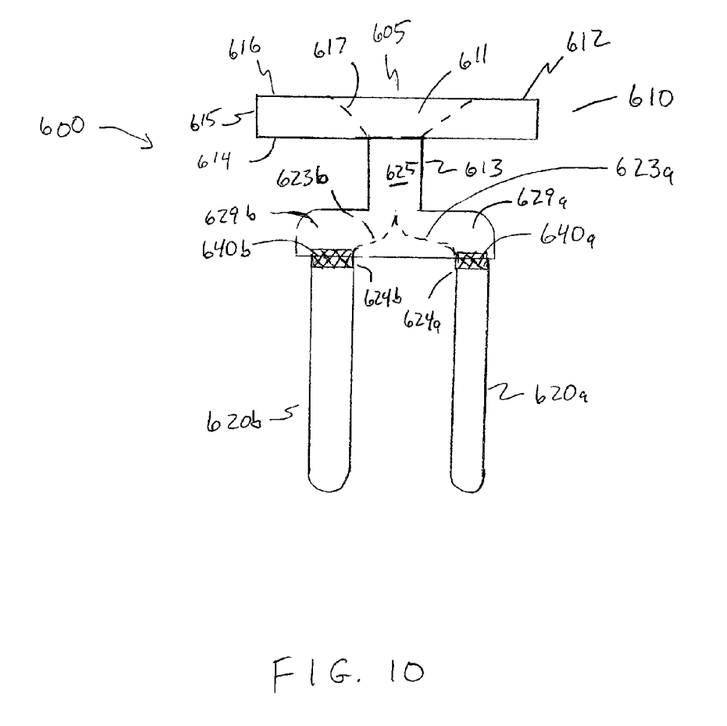
FIG. 10 shows a side view of a fifth embodiment.

Referring to FIG. 10, a fifth embodiment 600 is shown, including mouthpiece 610 having mouth contact portion 612, flow channel 605 including basin 611 with basin interior surface 617 in fluid communication with conduit interior channel 625. Mouth contact portion 612 includes first, second and third contact surfaces 614, 615 and 616, respectively. Conduit 613 includes a plurality of mating ports 624a and 624b, respectively, and includes collector channels 629a and 629b corresponding to mating ports 624a and 624b. Interior walls 623a and 623b extend into conduit 613 to define collector channels 629a and 629b. Collector channels 629a and 629b extend into conduit interior channel 625 along a portion of its length and direct saliva flow to their respective collectors 620a and 620b through their respective mating ports 624a and 624b.

Referring again to FIG. 10, a fifth embodiment includes filters 640a and 640b interposed between mouthpiece internal passage 605 and collectors 620a and 620b such that saliva flows through one or the other filter before entering its respective collector. In the embodiment filters 640a and 640b are disposed within mating ports 624a and 624b, respectively, between collection channels 629a and 629b and their respective collectors 620a and 620b. Filters 640a and 640b prevent food particles and large clumps of disrupted cells, which are largely composed of lipids and denatured protein, from entering into collectors 620a and 620b, while permitting individual cells and small clusters of intact cells to pass through. Such separation may be desired, for example, when the saliva sample is to be used in an assay in which large cell clumps and other debris would be expected to adversely affect the assay. Filter sizes and materials may be specified to differentiate between human and bacterial cells as well. A user may also specify different characteristics between filters 640a and 640b.

Figure 4:
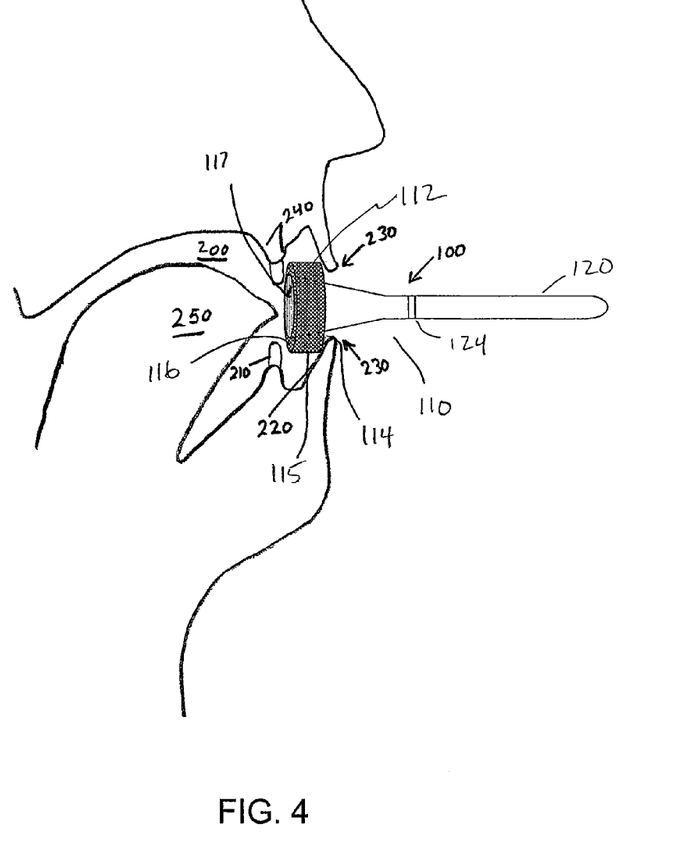
FIG. 4 shows cut away side view of a subject with a saliva collection device inserted into a the subject's mouth.
Figure 5:
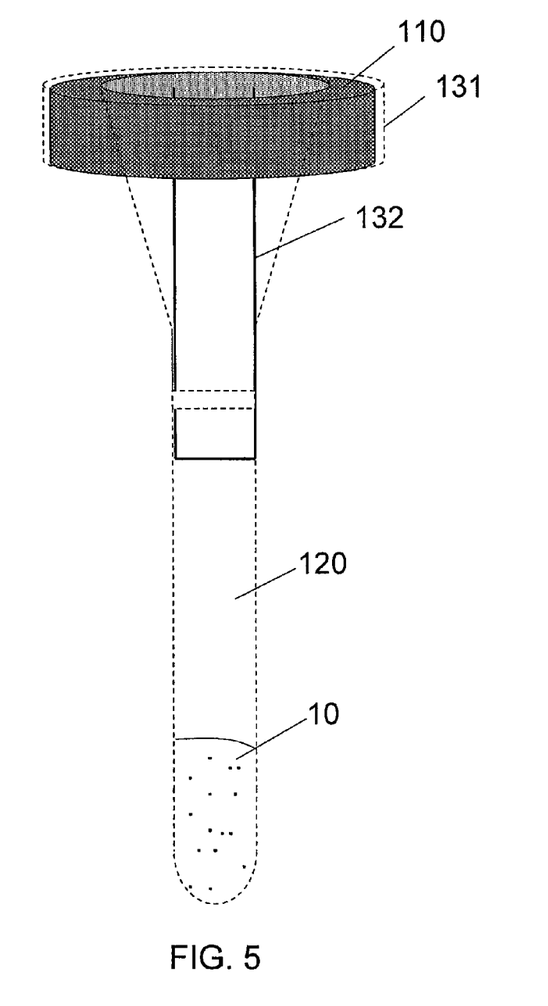
FIG. 5 shows a side view of a first embodiment with a closure member installed.
Figure 6:
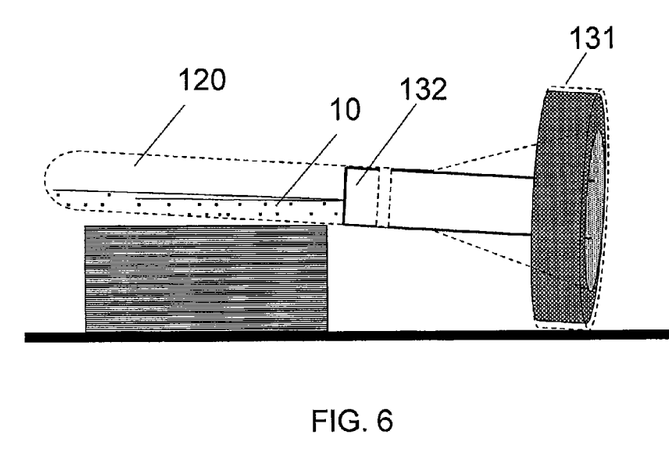
FIG. 6 shows a side view of a first embodiment with a closure member installed.

Referring to FIGS. 1-6, the operation of a first embodiment of a collection device 100 is demonstrated. As shown in FIG. 4, the device 100 is inserted into the mouth 200 of a subject so that mouthpiece 110 is inside mouth 200. Mouthpiece 110 is moved about and/or rotated inside the mouth 200 so as to bring mouth contact portion 112 in contact with the interior surfaces of mouth 200, such as the inner cheeks 220, lips 230, gums 240 and tongue 250. In the example, mouth contact portion 112 is shown placed outside the teeth 210, but may be inserted behind teeth 210 in order to contact the rear gums and roof of the mouth. Rubbing contact surfaces 114, 115 and 116 against the tissue surfaces releases buccal cells which accumulate in the subject's saliva to create a higher concentration of cellular material. Rotating Interior surface 117 of basin 111 against tongue 250 releases additional cells and stimulates saliva production. Mouthpiece 110 may be left within the subject's mouth to allow saliva to flow through flow channel 105 into conduit 113 and thence into collector 120. Alternatively, mouthpiece 110 may be removed after agitating and the subject may spit or drool into basin 111 for collection. When an adequate volume of saliva has been obtained, the device may be removed from the subject's mouth and either sealed using closure member 130, or collector 120 may be de-coupled and sealed. Mouth contact portion 112 may be sealed and retained for testing as well.

Referring to FIG. 9, it may be desirable to use a bent conduit 513 when working with a collector 520 which is pre-loaded with buffer or other solution, in order to prevent back flow into the subject's mouth.

Although the collection device thus far has been described as being used to collect a saliva sample from a human, it is to be understood, however, that the collection device is not limited to being used to collect a saliva sample from a human. For example, the collection device may be used to collect a saliva sample from a non-human animal, such as a monkey, chimpanzee, orangutan, gorilla, goat, bovine, equine, feline, canine, porcine or other vertebrate.

The collection device may be either disposable or re-usable and may be formed from any suitable materials, as determined by the needs of the user. For example, the collection device may be wholly or partially formed from plastic, such as polypropylene, polystyrene, polycarbonate, polyurethane, or polyethylene, or any combination thereof, or from glass and/or metallic materials. For example, the mouthpiece may be formed from stainless steel and the collector may be formed from glass. It may be advantageous to form the mouthpiece from a metal such as stainless steel when the mouthpiece is intended for non-human use, as non-human animals would be less likely to chew through or otherwise destroy a metal than they would a softer material, such as plastic. Further, although it is known that nucleic acids adhere to glass (and therefore glass may not be the best choice from which to form the collector when maximum DNA or RNA is to be obtained from the saliva sample), glass may be preferred where the saliva sample is to be used in certain applications, such as applications in which chemical reaction between the saliva sample or one or more components of the saliva sample and the material or materials used to form the collector is to be strictly avoided or minimized, for example.

The present saliva sample collection device or only the mouthpiece also may be included as part of a kit. In addition to the collection device or the mouthpiece, the kit may include instructions for using the collection device or the mouthpiece, wherein the instructions include at least a step of inserting all or a portion of the mouthpiece into an animal's mouth and a step of collecting a saliva sample there from. The instructions may be physically provided with the kit or a merely a description of how to otherwise access them, such as when the instructions are electronically provided on the Internet, may be provided with the kit. The kit optionally may further include one or more other components, such as the collector, the agent or agents, and the closure device. Further, the kit may include means, such as tear away plastic wrapping (which may encompass the mouthpiece 110 and cap 131 at region 133 of FIG. 3B), for example, for keeping at least the mouthpiece sanitary, and, if desired, sterile, during any storage and/or transit of the kit. A remote provider of genetic testing may wish to commercially offer the kit to the public as part of a business strategy that includes having a remote purchaser or other user of the kit collect the saliva sample in the collection device and then give the sample sealably retained in the collection device to the provider, such as by postal carrier, for example, for subsequent testing thereof. The kit packaging would also include bar coding for traceability reasons, instructions for use and return leak-proof packaging While the present invention has been described with particular reference to certain examples, it is to be understood that the present invention includes all reasonable equivalents thereof as defined by the following appended claims. Those skilled in the art will recognize that numerous modifications and changes may be made to the preferred embodiment without departing from the scope of the claimed invention. It will, of course, be understood that modifications of the invention, in its various aspects, will be apparent to those skilled in the art, some being apparent only after study, others being matters of routine mechanical, chemical and electronic design. No single feature, function or property of the preferred embodiment is essential. Other embodiments are possible, their specific designs depending upon the particular application. As such, the scope of the invention should not be limited by the particular embodiments herein described but should be defined only by the appended claims and equivalents thereof.

We claim:

1. A passive saliva sample collection device operable without need of a vacuum source, comprising:
   a mouthpiece having a toroidal mouth contact portion including an outer contact surface to go against the interior surfaces of a mouth, and a flow channel through said mouthpiece;
   a conduit coupled to said mouthpiece, said conduit having an interior channel in fluid communication with said flow channel; and,
   one or more collectors coupled to said conduit.

2. A passive saliva sample collection device operable without need of a vacuum source, comprising:
   a mouthpiece having a toroidal mouth contact portion including an outer contact surface to go against the interior surfaces of a mouth, and a flow channel through said mouthpiece;
   a conduit coupled to said mouthpiece, said conduit including an interior channel in fluid communication with said flow channel and one or more mating ports in fluid communication with said conduit interior channel; and, wherein each of said one or more mating ports is also removably couplable to a collector.

3. A device as in claim 2, further comprising one or more collectors corresponding to said one or more mating ports, each of said one or more collectors removably couplable to a corresponding mating port.

4. A device as in claim 2, wherein said flow channel comprises an open concave basin having a surface tapering from said outer contact surface inward to said conduit, the basin surface forming a continuous contact surface with the outer contact surface.

5. A device as in claim 2 or 4, further comprising: wherein said outer contact surface includes texturing.

6. A device as in claim 5, further comprising: wherein said texturing includes a plurality of parallel ridges.

7. A device as in claim 4, further comprising: wherein said basin surface includes texturing.

8. A device as in claim 2 or 4, further comprising: wherein said mouth contact portion outer surface includes at least opposing front and back contact surfaces, and said mouth contact portion further includes a plurality of internal channels extending through said mouth contact portion from said front contact surface to said back contact surface, said internal channels disposed around said flow channel.

9. A device as in claim 2 or 4, further comprising: wherein said mouth contact portion outer surface includes a plurality of external channels disposed around said flow channel.

10. A device as in claim 2 or 4, further comprising: wherein said one or more mating ports comprises a plurality of mating ports, and said conduit includes a plurality of collector channels corresponding to said plurality of mating ports, each of said plurality collector channels extending within at least a portion of said conduit interior channel, each of said plurality of collector channels in fluid communication with said conduit interior channel and one of said plurality of mating ports.

11. A device as in claim 2 or 4, further comprising:
a filter disposed between said mouthpiece flow channel and said one or more collectors, said filter in fluid communication with said conduit internal passage and said one or more mating ports.

12. A device as in claim 10, further comprising:
a plurality of filters corresponding to said plurality of mating ports, each of said filters disposed between a corresponding collector channel and a corresponding collector.

13. A device as in claim 3, further comprising preservation material disposed in at least one of said one or more collectors.

14. A device as in claim 1, further comprising:
a closure member, said closure member including a first portion sealing insertable into said conduit and a second portion enclosing said mouthpiece.

15. A passive saliva sample collection device operable without need of a vacuum source, comprising:
a mouthpiece having a toroidal mouth contact portion and a flow channel through said mouthpiece, wherein said mouth contact portion further comprises a textured outer contact surface, and said flow channel further comprises a basin having a textured interior surface tapering from said outer contact surface inward to said conduit;

a conduit coupled to said mouthpiece, said conduit including an interior channel in fluid communication with said flow channel and one or more mating ports in fluid communication with said conduit interior channel; and, one or more collectors corresponding to said one or more mating ports, each of said one or more collectors removably couplable to a corresponding mating port.

16. A device as in claim 15, further comprising:

at least one filter disposed between said flow channel and at least one of said one or more collectors.

* * * * *